United States Patent
Striegel et al.

(10) Patent No.: US 8,147,245 B2
(45) Date of Patent: Apr. 3, 2012

(54) ACOUSTICALLY ACTIVATED DENTAL INSTRUMENT

(75) Inventors: Marcus Striegel, Nürnberg (DE); Thomas Schwenk, Rückersdorf (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 96 days.

(21) Appl. No.: 12/502,919

(22) Filed: Jul. 14, 2009

(65) Prior Publication Data
US 2010/0009315 A1  Jan. 14, 2010

(30) Foreign Application Priority Data
Jul. 14, 2008 (DE) .......................... 10 2008 033 062

(51) Int. Cl.
*A61C 3/06* (2006.01)
(52) U.S. Cl. ........................................................ 433/166
(58) Field of Classification Search .................. 433/81, 433/102, 165, 166, 114, 118, 119, 143, 224, 433/141, 142
See application file for complete search history.

(56) References Cited

U.S. PATENT DOCUMENTS

| | | | |
|---|---|---|---|
| 3,919,775 A | 11/1975 | Malmin | |
| 5,971,758 A | 10/1999 | Hugo et al. | |
| 6,267,594 B1 | 7/2001 | Hugo | |
| 7,311,522 B2 * | 12/2007 | Graybill et al. | 433/102 |
| 7,481,652 B2 * | 1/2009 | Senia et al. | 433/102 |
| 2004/0126734 A1 * | 7/2004 | Senia et al. | 433/102 |
| 2004/0202981 A1 | 10/2004 | Luettgen et al. | |
| 2006/0068362 A1 * | 3/2006 | Desrosiers et al. | 433/102 |

FOREIGN PATENT DOCUMENTS

| | | |
|---|---|---|
| CN | 201070397 Y | 6/2008 |
| DE | 19752152 A1 | 6/1998 |
| DE | 202004019458 U1 | 3/2005 |
| EP | 0868887 B1 | 1/1998 |
| EP | 0868887 A2 | 10/1998 |
| EP | 0898941 A1 | 3/1999 |
| EP | 0962192 A1 | 12/1999 |
| JP | 04104815 U | 9/1992 |
| JP | 10211216 A | 8/1998 |
| JP | 11128247 A | 5/1999 |
| WO | W003070121 A1 | 8/2003 |

OTHER PUBLICATIONS

Oct. 27, 2009, Search Report from European Patent Office, in EP 09 00 846.8, which also claims priority to the German application DE 10 2008 033 062.0, which is the priority German application of this U.S. application.

Mar. 5, 2009, Office Action from German Patent Office, in DE 10 2008 033 062.0, which is the priority German application of this U.S. application.

* cited by examiner

*Primary Examiner* — Sunil K Singh
(74) *Attorney, Agent, or Firm* — Kolisch Hartwell, P.C.

(57) ABSTRACT

An acoustically activated dental instrument that comprises a working head attached to a shaft, the working head being covered with abrasive particles at its front end portion and having a spherical basic shape at its distal end, the outside of which is covered with abrasive particles. The working head is flattened at an upper side substantially up to a center plane of the spherical basic shape, and is flattened on the lower side opposite to the upper flattened side.

25 Claims, 2 Drawing Sheets

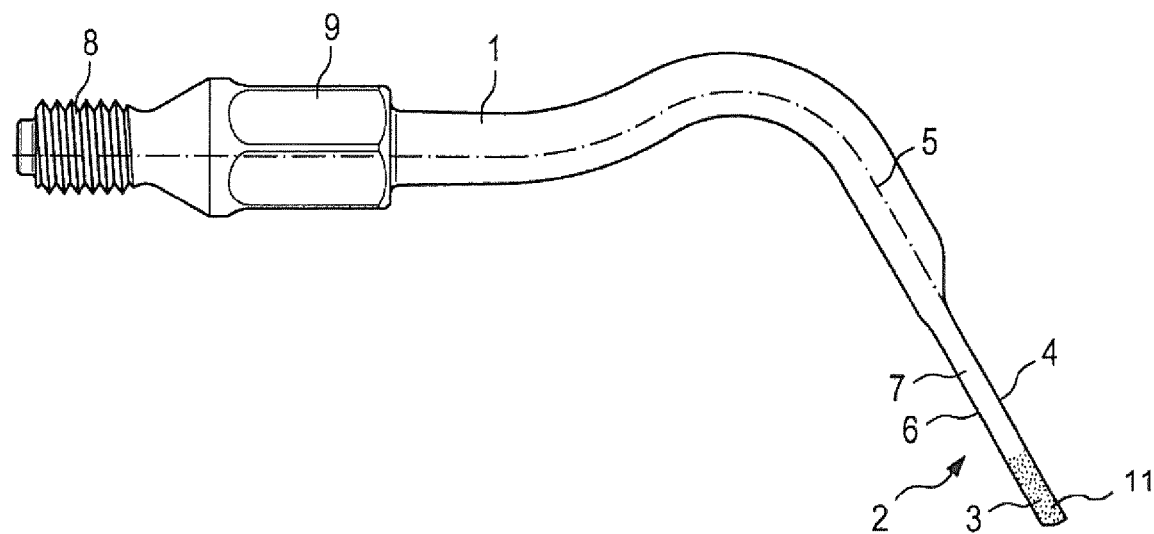
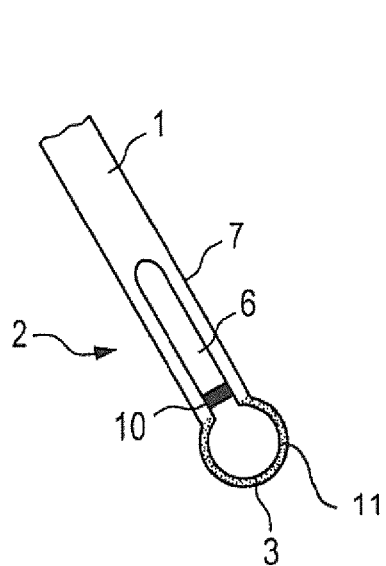 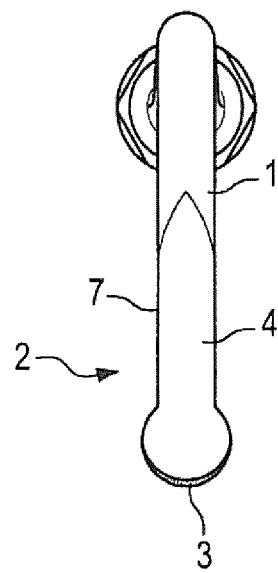
Fig. 1
Fig. 2  Fig. 3

ACOUSTICALLY ACTIVATED DENTAL INSTRUMENT

CROSS-REFERENCE TO RELATED APPLICATION

This application claims priority from German Patent Application Serial No. 10 2008 033 062.0, filed Jul. 14, 2008, which is incorporated herein by reference.

BACKGROUND

The invention relates to a dental instrument which can be activated by sound or ultrasound, the dental instrument comprising a working head which is attached to a shaft.

Instruments of that kind, which are also referred to as sonic tips, are commonly used for the fine preparation of teeth. They are in particular used in the approximal region of a tooth, at which said tooth is adjacent to a neighboring tooth. For the fine preparation, it is thus desired that the neighboring tooth is also processed by the dental instrument. Damages of respective neighboring teeth may therefore be avoided. For this reason, the dental instruments or sonic tips known from the state of the art are formed such that same are coated with abrasive material only on one side, such that the non-coated side is facing the neighboring tooth.

In particular for the minimal-invasive surgical crown extension, it is required to remove excessive bone material selectively without damaging the gingival rim or the tooth. This is not possible, or possible only to a small extent, with the dental instruments known from the state of the art.

SUMMARY

The invention relates to a dental instrument which can be activated by sound or ultrasound, the dental instrument comprising a working head which is attached to a shaft. At least partial regions of the working head are formed as an abrasive surface or are covered by abrasive particles, such as by, for example, diamond grains.

For example, in an embodiment, an acoustically activated dental instrument comprises a working head attached to a shaft, the working head being covered with abrasive particles at its front end portion and having a spherical basic shape at its distal end, the outside of which is covered with abrasive particles. The working head is flattened at an upper side substantially up to a center plane of the spherical basic shape, and is flattened on the lower side opposite to the upper flattened side.

BRIEF DESCRIPTION OF THE DRAWINGS

FIG. 1 is a lateral view of a first embodiment.

FIG. 2 is a left-side view, in relation to FIG. 1, of a working head.

FIG. 3 is a right-side view, in relation to FIG. 1, of the working head.

DETAILED DESCRIPTION

Figure 4:
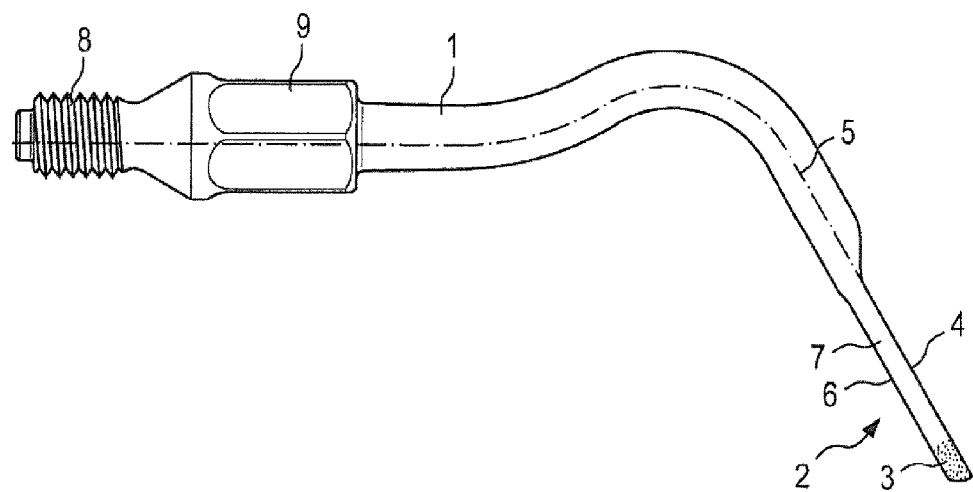
FIGS. 4 to 6 are analogous views of FIGS. 1 to 3 of a further embodiment.

In the following, the invention is described based on the non-exclusive, illustrative embodiments shown in the Figures. In the embodiments, identical components are designated with identical reference numerals.

The dental instrument, shown in the embodiments of FIGS. 1 and 4, has a thread 8 at its end portion, which can be screwed into a connector in the usual manner. For this purpose, a multi-sided tool 9 is used. Further, the dental instrument comprises a shaft 1 which has a substantially circular cross-section and is bent in a suitable manner.

A head or working head 2 is formed at the end of the shaft 1, which comprises a web or flattened web 7 as well as spherical or spherical layer-wise basic shape 3 at the distal end thereof.

The web 7 as well as the spherical basic shape 3 are flattened at an upper side 4 toward a center plane 5. The web 7 is not covered with abrasive particles, only the spherical or spherical layer-wise basic shape comprises abrasive particles 11.

Opposite to the upper side 4, a lower side 6 is provided, which is also flattened.

Figures 5, 6, 7:
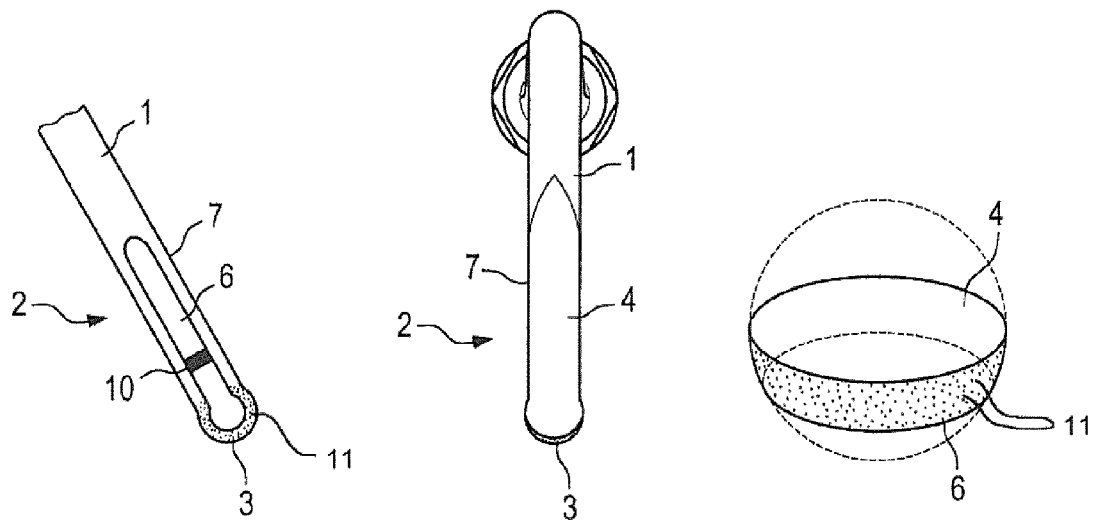
FIG. 7 is a schematic view of the basic shape of a spherical layer or spherical zone.

FIG. 7 shows a simplified illustration of a spherical layer or spherical zone, which is formed at the distal end of the working head 2 by the spherical or spherical layer-wise basic shape 3. Therewith, a spherical layer, spherical layer-wise, or spherical zone are covered with abrasive particles 11 on its outside formed by the spherical basic shape is generated. The flattened portions of the spherical layer or spherical zone are not covered with abrasive particles, as it is shown in the Figures.

In some embodiments, the invention relates to an acoustically activated dental instrument, comprising a working head 2 attached to a shaft 1, which working head is covered with abrasive particles 11 at its front end portion, wherein the working head 2 has a spherical basic shape 3 at its distal end, the outside of which is covered with abrasive particles 11, wherein the working head 2 is flattened at an upper side 4 thereof, in relation to a center plane of the sphere substantially to the center plane, and wherein the working head 2 is flattened on the lower side 6 opposite to the upper flattened side 4.

It is an object underlying the present invention to provide a dental instrument of the aforementioned kind, which is particularly suited for a surgical crown extension while having a simple structure and a simple and cost-effective design.

According to the invention, it is thus provided that a spherical basic shape is formed at the distal end of the working head of the dental instrument, the outside of which is coated with abrasive particles. The spherical basic shape is flattened on both sides, such that there results the shape of a spherical layer or spherical zone. Therewith, the working head comprises upper and lower flattened sides which are respectively formed flat and are not covered with abrasive particles. Also the remaining region of the working head is not covered with abrasive particles.

The surgeon or dentist may therefore remove bone material in a very precise manner, without any danger to hurt the gingival rim, the tooth or the gingival. Consequently, a particularly precise preparation is possible.

In a preferred (but not required) embodiment of the invention, it is provided that the shaft and the spherical layer of the semi-spherical or drop-shaped basic shape of the distal end of the working head is flattened toward a center plane of the sphere and the end portion of the shaft. Therewith, there results the shape of a semi-sphere, the other side of which is also flattened. Thus, the basic shape has a diameter in the region of the flattened upper plane, which is equal to the diameter of the sphere.

The shaft preferably (but not necessarily) has a substantially circular cross-section and thus forms, due to the flattened portions on both sides, a flat web in the distal portion of the working head. This web, together with the spherical layer-wise end shape, preferably (but not necessarily) has a substantially equal thickness. The equal thickness is preferably (but not necessarily) formed continuously.

Further, it has proven to be advantageous if the flattened upper side and the flattened lower side are respectively formed planar. In this context, it is preferred (but not required) that both planar sides are parallel to each other or extend slightly conically and/or are formed flush. In addition, it is possible to coat the flattened sides with a hard layer, such as, for example, made of titanium nitride (TiN) or zirconium dioxide ($ZrO_2$).

The spherical basic shapes according to the invention may, for example, have a diameter in the range of 1.5 to 4 mm. Preferred (but not required) diameters range between 2.0 and 3.0 mm.

The thickness of the flattened portion preferably (but not necessarily) ranges between 0.5 and 1 mm, and is preferably (but not necessarily) 0.8 mm.

Referring to FIGS. 2 and 5, a depth marking 10 is formed with a distance of, for example, 3 mm from the distal end of the spherical basic shape 3, for example, by means or way of a laser engraving or the like.

According to the invention, it is further preferred (but not required) that the working head is provided with at least one depth marking. By means or way of the inventive dental instrument, the excessive bone may be removed during a surgical crown extension—as far as this is required for aesthetic or functional reasons—such that the crowns have equal lengths in the visible region. In this context, it is important that an area of approx. 3 mm is generated between the crown rim and the gingival rim.

By means or way of the aforementioned depth marking, it is thus possible in a particularly preferred (but not required) manner to inform the user in a simple way as soon as the desired depth below the gingival, e.g., 3 mm, is reached during the preparation, for example by applying a marking at a distance of 3 mm from the distal end of the working head.

With the inventive dental instrument, a surgical crown extension can be performed simply, fast, and gently.

Compared to the dental instruments (sonic tips) known from the state of the art, the inventive dental instrument is hence flattened on both sides and covered with abrasive particles (e.g., diamond grains) only at the distal end of the head. The abrasive basic shape is therefore part of a sphere, i.e. a spherical layer or spherical zone, wherein the spherical layer or spherical zone is flattened toward the center of the basic shape of the sphere.

We claim:

1. An acoustically activated dental instrument comprising a working head attached to a shaft, the working head having a web portion and a spherical frustum-shaped portion at a distal end of the web portion, the outside of the spherical frustum-shaped portion being covered with abrasive particles, wherein the working head is flattened at an upper side substantially down to a center plane of the shaft, such that a center plane of the working head is off center relative to the center plane of the shaft, further wherein the spherical frustum-shaped portion has a flat top surface and a flat bottom surface that form a pair of parallel planes, and a diameter greater than a diameter of the web portion.

2. The dental instrument of claim 1, wherein the shaft has a substantially circular cross section and is formed in the shape of a flat web in the region of the working head.

3. The dental instrument of claim 2, wherein the spherical frustum-shaped portion and the flat web portion have an identical thickness.

4. The dental instrument of claim 2, wherein the spherical frustum-shaped portion and the flat web portion have a continuous thickness.

5. The dental instrument of claim 1, wherein the working head is flattened on a lower side opposite to the upper flattened side, and the flattened upper side and the flattened lower side are formed parallel to each other.

6. The dental instrument of claim 1, wherein the working head is flattened on a lower side opposite to the upper flattened side, and the flattened upper side and the flattened lower side are respectively formed flush with the flat top surface and the flat bottom surface of the spherical frustum-shaped portion.

7. The dental instrument of claim 1, wherein the working head includes at least one depth marking.

8. An acoustically activatable dental instrument comprising a working head attached to a shaft that is adapted to be fixedly attached to an acoustical actuator, the working head having a web portion and a spherical frustum-shaped portion at a distal end of the web portion, an outside surface of the spherical frustum-shaped portion being covered with abrasive particles, wherein the working head is flattened at an upper side substantially down to a center plane of the shaft, and is flattened on a lower side opposite to the upper flattened side, wherein the flattened upper side and the flattened lower side form a pair of parallel planes that define a flat top surface and a flat bottom surface of the spherical frustum-shaped portion, further wherein a diameter of the spherical frustum-shaped portion is larger than a diameter of the web portion and intersects the flat top and bottom surfaces.

9. The dental instrument of claim 8, wherein the flattened upper side and the flattened lower side are formed parallel to each other.

10. The dental instrument of claim 8, wherein the flattened upper side and the flattened lower side are respectively formed flush with the flat top surface and the flat bottom surface of the spherical frustum-shaped portion.

11. The dental instrument of claim 8, wherein the shaft has a substantially circular cross section and is formed in the shape of a flat web in the region of the working head.

12. The dental instrument of claim 11, wherein the spherical frustum-shaped portion and the flat web have an identical thickness.

13. The dental instrument of claim 1, wherein the working head includes at least one depth marking.

14. The dental instrument of claim 8, wherein the shaft includes at least one bend, and the working head forms a fixed oblique angle with respect to the shaft.

15. The dental instrument of claim 8, further including a threaded portion at a first end of the shaft opposite a second end of the shaft, the second end being proximate the working head.

16. The dental instrument of claim 8, wherein a diameter of the flat top surface of the spherical frustum-shaped portion is greater than a diameter of the flat bottom surface of the spherical frustum-shaped portion.

17. The dental instrument of claim 16, wherein each diameter is in the range of about 1.5 mm to about 4.0 mm.

18. The dental instrument of claim 2, wherein each continuous thickness is in the range of about 0.5 mm to about 1.0 mm.

19. An acoustically activated dental instrument comprising a shaft including a first end and a working head at a second end;

wherein the working head includes an upper surface flattened substantially to a center plane of the shaft such that a center plane of the working head is off center relative to the center plane of the shaft, and a web portion connected to a spherical frustum-shaped portion at a distal end of the web portion, wherein the spherical frustum-shaped portion has an outer surface covered in abrasive particles, a flat top surface and a flat bottom surface that form a pair of substantially parallel planes, and a diameter greater than a diameter of the web portion.

20. The dental instrument of claim 19, wherein the first end includes a threaded portion.

21. The dental instrument of claim 19, wherein each of the flat top and bottom surfaces extends across the diameter of the spherical frustum-shaped portion from proximate a distal end of the working head to proximate the distal end of the web portion, and the top and bottom surfaces form a pair of parallel planes.

22. The dental instrument of claim 19, wherein the web portion is sized and connected to the spherical frustum-shaped portion such that a circumference of the flat top surface of the spherical frustum-shaped portion forms substantially more than half of a circle.

23. The dental instrument of claim 22, wherein a diameter of the flat top surface of the spherical frustum-shaped portion is greater than a diameter of the flat bottom surface of the spherical frustum-shaped portion.

24. The dental instrument of claim 19, wherein a surface of the web portion is covered in abrasive particles.

25. The dental instrument of claim 19, wherein the center plane of the working head is off center relative to the center plane of the shaft in a direction away from the upper surface and toward the lower surface of the working head.

* * * * *